US011376252B2

(12) United States Patent
Tang-Liu et al.

(10) Patent No.: US 11,376,252 B2
(45) Date of Patent: *Jul. 5, 2022

(54) MULTIKINASE INHIBITORS AND USES IN PROSTATIC HYPERPLASIA AND URINARY TRACK DISEASES

(71) Applicant: AIVIVA BIOPHARMA, INC., Las Vegas, NV (US)

(72) Inventors: Diane Dan-shya Tang-Liu, Las Veas, NV (US); Tiffany Constance Liu, Las Vegas, NV (US); Gerald Woodrow Devries, San Clemente, CA (US)

(73) Assignee: AIVIVA BIOPHARMA, INC., Las Vegas, NV (US)

(*) Notice: Subject to any disclaimer, the term of this patent is extended or adjusted under 35 U.S.C. 154(b) by 81 days.

This patent is subject to a terminal disclaimer.

(21) Appl. No.: 16/958,605

(22) PCT Filed: Dec. 30, 2017

(86) PCT No.: PCT/US2017/069166
§ 371 (c)(1),
(2) Date: Jun. 26, 2020

(87) PCT Pub. No.: WO2019/133022
PCT Pub. Date: Jul. 4, 2019

(65) Prior Publication Data
US 2020/0352943 A1    Nov. 12, 2020

(51) Int. Cl.
| | | |
|---|---|---|
| *A61K 31/47* | (2006.01) | |
| *A61K 9/00* | (2006.01) | |
| *A61K 31/5025* | (2006.01) | |
| *A61K 31/404* | (2006.01) | |
| *A61K 31/44* | (2006.01) | |
| *A61K 31/496* | (2006.01) | |
| *A61K 31/506* | (2006.01) | |

(52) U.S. Cl.
CPC ........ *A61K 31/5025* (2013.01); *A61K 31/404* (2013.01); *A61K 31/44* (2013.01); *A61K 31/47* (2013.01); *A61K 31/496* (2013.01); *A61K 31/506* (2013.01); *A61K 9/0019* (2013.01); *A61K 9/0031* (2013.01)

(58) Field of Classification Search
CPC ................. A61K 31/47; A61P 13/08
See application file for complete search history.

(56) References Cited

U.S. PATENT DOCUMENTS

| | | | | |
|---|---|---|---|---|
| 2009/0005767 A1* | 1/2009 | Moran | ................ | A61B 18/22 606/10 |
| 2012/0178707 A1* | 7/2012 | Cao | .................. | A61K 31/44 514/35 |

FOREIGN PATENT DOCUMENTS

| | | | |
|---|---|---|---|
| CN | 107019697 A | 8/2017 | |
| WO | WO-2004062666 A2 * | 7/2004 | ............ A61P 13/08 |
| WO | 2009143101 A2 | 11/2009 | |
| WO | 2017062694 A1 | 4/2017 | |
| WO | 2017207534 A1 | 12/2017 | |
| WO | 2019036367 A1 | 2/2019 | |

OTHER PUBLICATIONS

Andersson (Current Opinion in Urology vol. 25 pp. 12-18, published 2015) (Year: 2015).*
Matsui (International Journal of Cancer, vol. 122 pp. 664-671 published 2008) (Year: 2008).*
Ishizaki (Molecular Pharmacology Vo. 57, pp. 976-983 published 2000) (Year: 2000).*
International Search Report and Written Opinion, PCT/US2017/069166, dated Mar. 8, 2018.
Hatano, T. et al., "Shrinkage of Prostate Volume in Sunitinib-treated Patients with Renal Cell Carcinoma" Japanese Journal of Clinical Oncology (2013) vol. 43, No. 12, pp. 1282-1285.
Bono, A. V. et al., "Sorafenib's inhibition of prostate cancer growth in transgenic adenocarcinoma mouse prostate mice and its differential effects on endothelial and pericyte growth during tumor angiogenesis" Analytical and Quantitative Cytology and Histology, (Jun. 2010) vol. 32, No. 3, pp. 136-145 & Medline abstract 2010741361.
Mirantes, C. et al., "Effects of the multikinase inhibitors Sorafenib and Regorafenib in PTEN deficient neoplasias" European Journal of Cancer, vol. 63, pp. 74-87, 2006.
Ozgur-Akdemir, A. et al., "Imatinib Mesylate (Gleevec) as Protein-tyrosine Kinase Inhibitor Elicits Smooth Muscle Relaxation in Isolated Human Prostatic Tissue" Urology (2011) vol. 78, No. 4, pp. 968.e1-968.e6.
Peng, J. et al., "Effect of PI3K/AKT inhibitor on benign prostate hyperplasia and its mechanism: an experimental study" Zhonghua Nan Ke Xue. (2010) vol. 16, No. 12 pp. 1068-1075.
Liu, F. et al., "Nintedanib, a triple tyrosine kinase inhibitor, attenuates renal fibrosis in chronic kidney disease" Clinical Science (Jul. 2017) vol. 131, issue 16, pp. 2125-2143.

(Continued)

*Primary Examiner* — Theodore R. Howell
*Assistant Examiner* — George W Kosturko
(74) *Attorney, Agent, or Firm* — Maschoff Brennan; Brent A. Johnson; David Old

(57) ABSTRACT

A method for preventing, treating and/or improving a prostatic disease or disorder associated with epithelial hyperplasia and/or fibrosis, comprising: administering an effective amount of a multikinase inhibitor to a subject in need thereof, wherein the multikinase inhibitor has a certain spectrum of kinase inhibitory activity. The multikinase inhibitor is sunitinib, regorafenib, ponatinib, pazopanib, nintedanib and/or lenvatinib. The prostatic disease or disorder is selected from the group consisting of benign prostate hyperplasia and its associated lower urinary tract symptoms, fibrosis of ureters and renal pelvis, prostate adenoma, and prostatic intraepithelial neoplasia in animals and humans.

11 Claims, 6 Drawing Sheets

(56) References Cited

OTHER PUBLICATIONS

Extended European Search Report for related application EP 17936520.0, dated Sep. 16, 2021.

Noguiera, P. E. et al., "Nintedanib delays prostate dorsolateral lobe cancer progression in the TRAMP model: contribution to the epithelial-stromal interaction balance" Cell Biology International, 42(2), 153-168, Feb. 2018.

* cited by examiner

MULTIKINASE INHIBITORS AND USES IN PROSTATIC HYPERPLASIA AND URINARY TRACK DISEASES

CROSS-REFERENCE TO RELATED APPLICATIONS

This application is a national phase application of PCT/US2017/069166, filed on Dec. 30, 2017, which is incorporated by reference herein in its entirety.

FIELD OF THE INVENTION

The invention relates to compounds that possess a certain spectrum of multikinase inhibition activities, which act on specific growth factor and/or cytokine signaling pathways and or phases of responses in urinary tract diseases.

BACKGROUND OF THE INVENTION

Benign prostatic hyperplasia (BPH) and its associated lower urinary tract symptoms (LUTS) are common in aging men. Histopathologically, BPH is characterized by an increased number of epithelial and stromal cells in the periurethral portion of the prostate. This is manifest by the appearance of microscopic nodules which progressively proliferate and enlarge to increase the mass of both the glandular and stromal prostatic tissue.

Testosterone has been proposed to be involved in the development of BPH. In the prostate, the nuclear membrane bound enzyme 5alpha-reductase converts the hormone testosterone to dihydrotestosterone (DHT). That DHT is important in causing hyperplasia is supported by the clinical observation that inhibition of 5alpha-reductase can reduce DHT levels by as much as 85%-90% in the prostate and, in turn, reduce prostate volume and BPH symptoms. 5alpha-reductase inhibitors, such as finasteride and dutasteride, have been used to treat BPH worldwide.

The proliferation of stromal cells in BPH is a major contributor to development of this disease. Active smooth muscle tone is regulated by the adrenergic nervous system. Stimulation of the alpha1-adrenergic receptors mediates active tension in prostatic smooth muscle and results in an increase in prostatic urethral resistance. Alpha1-adrenoceptor antagonists, such as tamsulosin and alfuzosin, can relieve urethral obstruction associated with BPH.

The use of 5alpha-reductase inhibitors are slow-acting, associated with sexual side effects. Alpha1-adrenoceptor antagonists are more effective and fast acting, but can produce vasodilator side effects. Furthermore, these pharmacotherapies are primarily effective in mild to moderate stages of the disease. There is a clear need for improved pharmacotherapy for benign prostatic hyperplasia and lower urinary tract symptoms.

Prostate cancer is mostly a very slow progressing disease and starts in the gland cells. The prostate cancer starts with tiny alterations in the shape and size of the prostate gland cells—Prostatic intraepithelial neoplasia (PIN). Nearly 50% of all 50-year-old men have PIN. Any patient who was found to have high-grade PIN after a prostate biopsy is at a significantly greater risk of having cancer cells in his prostate.

A number of growth factors and cytokines have been implicated in the development of BPH and/or PIN. It has been argued that members of the FGF, IGF and TGF families, in particular, contribute to the progression of BPH. Staining for VEGF, VEGFR-1, VEGFR-2 and CD105 positive microvessels was reported in human BPH tissues. This suggests an active role for VEGF in the pathological process of BPH.

These data suggest that regulation of growth factor and cytokine signaling pathways through the use of multikinase receptor inhibitors would be a novel strategy for the prevention and/or treatment of proliferative and fibrotic disorders of prostate and urinary tract and their associated symptoms.

SUMMARY OF THE INVENTION

Embodiments of the invention provide agents that possess a certain spectrum of multikinase inhibitor activities and are useful in the treatment of prostatic disease or disorder associated with epithelial hyperplasia and/or fibrosis, comprising: administering an effective amount of a multikinase inhibitor to an animal or human. Embodiments of the invention are also directed to the therapeutic or prophylactic uses of such compounds and compositions, and to methods for treating prostatic disease or disorder associated with epithelial hyperplasia and/or fibrosis.

In one aspect, the invention provides agents which possess a certain spectrum of multikinase inhibitor activities and are accordingly useful in methods of treatment of disease states and/or disorders associated with benign prostate hyperplasia or lower urinary tract symptoms in humans. More specifically, the invention is also directed to the therapeutic or prophylactic uses of such compounds and compositions, and to methods of treating disease states and/or disorders associated with benign prostate hyperplasia and its associated lower urinary tract symptoms, fibrosis of ureters and renal pelvis, prostate adenoma, and prostatic intraepithelial neoplasia.

In one aspect, the invention provides a method for treating/preventing benign prostate hyperplasia and its associated lower urinary tract symptoms by administering a therapeutically effective amount of a multikinase inhibitor to a human subject in need of such treatment or prevention, wherein the multikinase inhibitor may include, but not limited to, sunitinib, regorafenib, ponatinib, pazopanib, nintedanib and lenvatinib. The prostatic disease or disorder is selected from the group consisting of benign prostate hyperplasia and its associated lower urinary tract symptoms, fibrosis of ureters and renal pelvis, prostate adenoma, and prostatic intraepithelial neoplasia in animals and humans.

DETAILED DESCRIPTION

Figure 1:
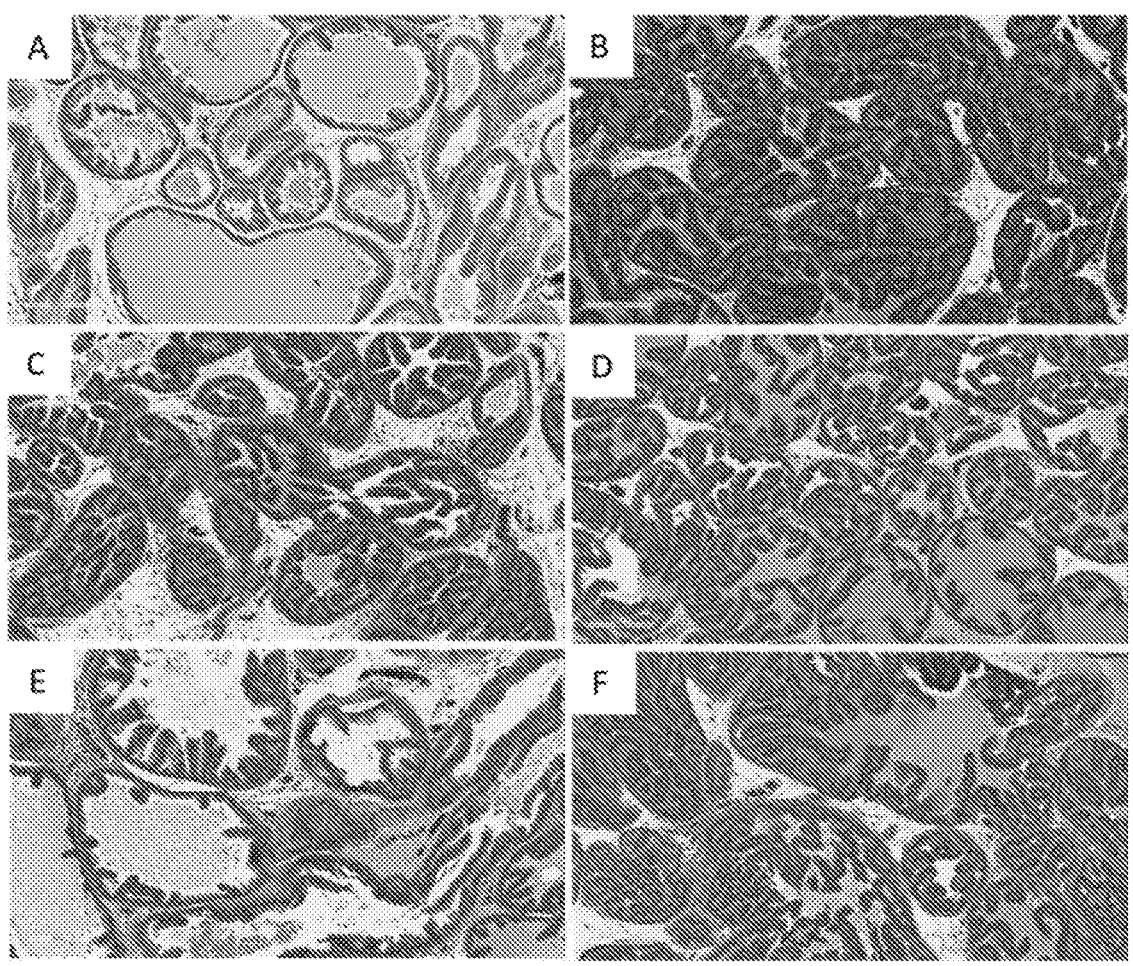
FIG. 1 shows microscope images of glandular hyperplasia in rat dorsolateral prostate at 100× magnifications. Panel (A) is a vehicle-treated sample, showing a normal (score=0) glandular profile. Panel (B) is a testosterone (TE) and phenylephrine (PE) induced and vehicle-treated sample, showing marked (score=4) epithelial hyperplasia. Panel (C) is a TE and PE induced and nintedanib-treated sample, showing moderate (score=3) epithelial hyperplasia. Panel (D) is a TE and PE induced and sunitinib-treated sample, showing moderate (score=3) epithelial hyperplasia. Panel (E) is a TE and PE induced and lenvatinib-treated sample, showing slight (score=2) epithelial hyperplasia. Panel (F) is a TE and PE induced and doxazosin-treated sample, showing moderate (score=3) epithelial hyperplasia.

Embodiments of the invention relate to preventing and/or treating diseases or disorders associated with benign prostate hyperplasia or its associated lower urinary tract symptoms, fibrosis of ureters and renal pelvis, prostate adenoma, and prostatic intraepithelial neoplasia in animals and humans. In accordance with embodiments of the invention, a method for treating benign prostate hyperplasia or its associated lower urinary tract symptoms may involve giving to a subject in need of such treatments a composition comprising a multikinase inhibitor that has a select spectrum of activities to inhibit select kinases such as VEGF and TGF beta.

A composition of the invention may comprise a multikinase inhibitor or a pharmaceutically acceptable salt thereof. As used herein, the term "multikinase inhibitor" refers to an inhibitor that can inhibit multiple kinases. As used herein, the term "pharmaceutically acceptable salts" refer to derivatives of the disclosed compounds wherein the parent compound is modified by making acid or base salts thereof.

Examples of pharmaceutically acceptable salts include, but are not limited to, mineral or organic acid salts of basic residues such as amines; alkali or organic salts of acidic residues such as carboxylic acids; and the like. The pharmaceutically acceptable salts include the conventional non-toxic salts or the quaternary ammonium salts of the parent compounds/molecules formed, for example, from non-toxic inorganic or organic acids. For example, such conventional non-toxic salts may include those derived from inorganic acids such as hydrochloric acid.

In accordance with some embodiments, the present invention also includes pharmaceutical compositions which contain, as an active ingredient, one or more of the compounds/molecules of the invention herein together with at least one pharmaceutically acceptable carrier, diluent or excipient.

In some embodiments, compounds/molecules of the present invention may be administered by parenteral, intramuscular, intradermal, subcutaneous, topical, intraperitoneal, intralesional, perilesional, intraprostatic, periprostatic, transrectal, and transurethral routes.

The dosage will depend on the route of administration, the severity of the disease, age and weight of the patient and other factors normally considered by the attending physician, when determining the individual regimen and dosage level as the most appropriate for a particular patient. That is, a therapeutically effective amount would be based on the patient (age, weight, etc.), the disease conditions, the route of administration, etc. One skilled in the art would be able to determine a therapeutically effective amount without inventive efforts.

In accordance with embodiments of the invention, the administration regimen could be before (induction) surgery, post-surgery (at or before trauma/acute inflammation, proliferation, remodeling, through maturation).

In accordance with embodiments of the invention, for preparing pharmaceutical compositions from the compounds/molecules of this invention, inert, pharmaceutically acceptable carriers can be either solid or liquid.

The term composition is intended to include the formulation of the active component or a pharmaceutically acceptable salt with a pharmaceutically acceptable carrier. For example, this invention may be formulated by means known in the art into the form of, for example, aqueous or oily solutions, suspensions, emulsions, creams, ointments, gels, and for parenteral use sterile aqueous or oily solutions or suspensions or sterile emulsions.

Liquid form compositions include solutions, suspensions, and emulsions. Sterile water or water-propylene glycol solutions of the active compounds/molecular may be mentioned as an example of liquid preparations suitable for parenteral administration. Liquid compositions can also be formulated in solution in aqueous polyethylene glycol solution. Aqueous solutions for oral administration can be prepared by dissolving the active component in water and adding suitable colorants, flavoring agents, stabilizers, and thickening agents as desired. Aqueous suspensions for oral use can be made by dispersing the finely divided active component in water together with a viscous material such as natural synthetic gums, resins, methyl cellulose, sodium carboxymethyl cellulose, and other suspending agents known to the pharmaceutical formulation art.

The pharmaceutical compositions can be in unit dosage form. In such form, the composition is divided into unit doses containing appropriate quantities of the active component. The unit dosage form can be a packaged preparation, the package containing discrete quantities of the preparations.

Compositions may be formulated for any suitable route and means of administration. Pharmaceutically acceptable carriers or diluents include those used in formulations suitable for rectal, topical or parenteral administration. The formulations may conveniently be presented in unit dosage form and may be prepared by any of the methods well known in the art of pharmacy.

For solid compositions, conventional non-toxic solid carriers include, for example, pharmaceutical grades of mannitol, lactose, cellulose, cellulose derivatives, starch, magnesium stearate, sodium saccharin, talcum, glucose, sucrose, magnesium carbonate, and the like may be used. Liquid pharmaceutically administrable compositions can, for example, be prepared by dissolving, dispersing, etc., an active compound/molecular as defined above and optional pharmaceutical adjuvants in a carrier, such as, for example, water, saline aqueous dextrose, glycerol, ethanol, and the like, to thereby form a solution or suspension. If desired, the pharmaceutical composition to be administered may also contain minor amounts of non-toxic auxiliary substances such as wetting or emulsifying agents, pH buffering agents and the like, for example, sodium acetate, sorbitan monolaurate, triethanolamine sodium acetate, sorbitan monolaurate, triethanolamine oleate, etc. Actual methods of preparing such dosage forms are known, or will be apparent, to those skilled in this art.

Embodiments of the invention will be illustrated with the following examples. One skilled in the art would appreciate that these examples are for illustration only and that other modifications and variations are possible without departing from the scope of the invention.

Example 1

Despite morphological and anatomical differences between prostate glands in humans and rodents, there are many similarities with regard to their pharmacology and histochemistry that make study of BPH in rats a useful investigative approach. The prostate gland in both humans and rats is innervated by fine networks surrounding the glandular elements. Most of these neural structures are catecholaminergic and contain different subtypes of adrenergic receptors.

Because of the potential effect of adrenergic innervation on the growth of prostatic cells, the effects of phenylephrine administration on the prostate in rats have been examined. At a dose of 1 mg/kg per day, phenylephrine induces irregular ducts with intraluminal projections. The epithelium becomes thicker and there are even focal "piling-up" of cells. The stroma, in turn, demonstrates hyperplasia and hypertrophy of fibrocytes and smooth muscle cells. These changes correspond to the entity of benign prostatic hyperplasia in humans. In addition, phenylephrine has a dual role in the development of PIN lesions affecting both epithelial and stromal constituents of the rat prostate.

BPH is a true hyperplastic process. Histologic studies have documented an increase in cell number. A study was conducted, therefore, to determine the effects of test compounds and vehicle on testosterone (TE) and phenylephrine (PE) induced benign prostate hyperplasia in rats. Male Wistar rats were induced with testosterone (2 mg/kg) plus phenylephrine (5 mg/kg) administered daily by subcutaneous injection on days 5 through 32. Vehicle or test compounds (all at 1% w/w), nintedanib, sunitinib, lenvatinib, and 0.5% doxazosin mesylate, were administered by intra-prostate injection (0.4 ml) in dorsolateral and ventral lobes on days 1 and 18. Animals were euthanized on day 32. Body weights were determined and prostate glands were harvested. The experimental design is outlined in Table 1.

TABLE 1

Study Design Outline

| Group* (Test Article) | Dose (mg) | Route of Administration | Day(s) of Administration | Animal Numbers |
|---|---|---|---|---|
| 1 (Vehicle) | 0 | Intra-prostate | 1, 18 | 6 |
| 2 (nintedanib) | 4 | Intra-prostate | 1, 18 | 6 |
| 3 (sunitinib) | 4 | Intra-prostate | 1, 18 | 6 |
| 4 (lenvatinib) | 4 | Intra-prostate | 1, 18 | 6 |
| 5 (doxazosin) | 2 | Intra-prostate | 1, 18 | 6 |
| 6 (Vehicle) | 0 | Intra-prostate | 1, 18 | 6 |

*All animals received testosterone (TE) and phenylephrine (PE), except Group 1.

Figure 3:
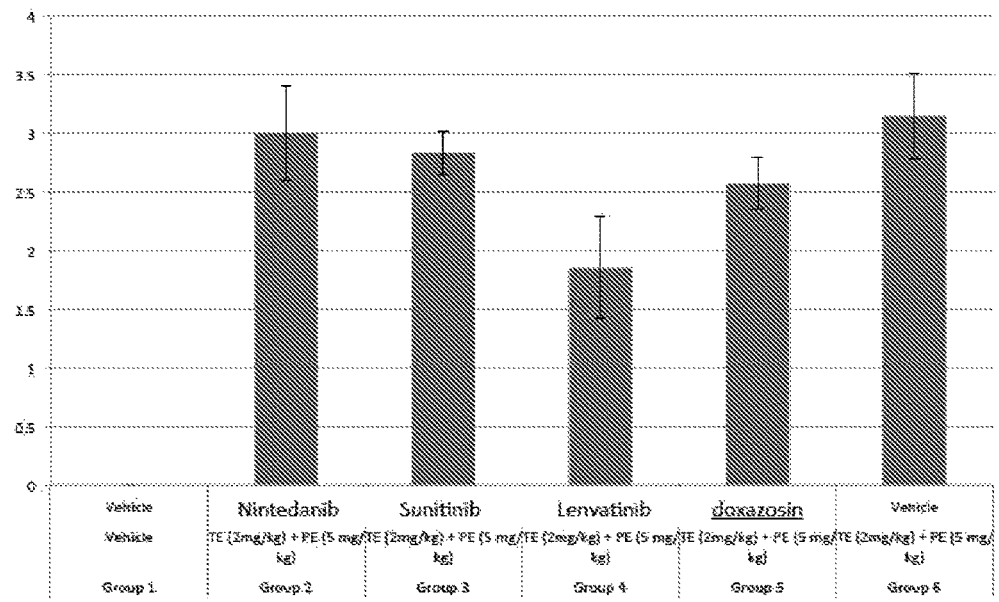
FIG. 3 shows glandular hyperplasia mean scores in dorsolateral prostate for the experiments described in FIG. 1.
Figure 4:
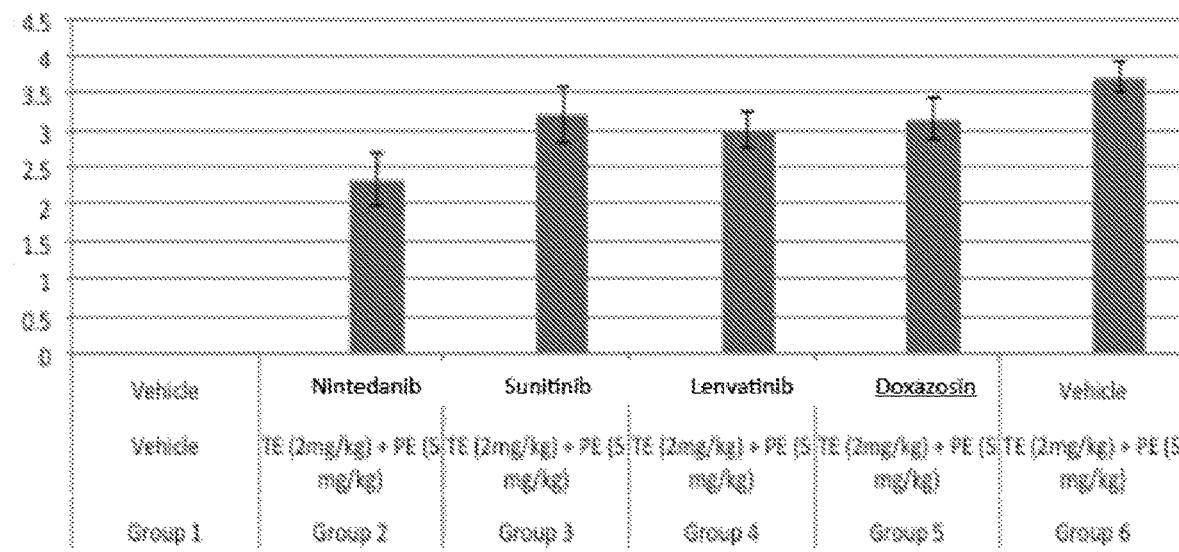
FIG. 4 shows glandular hyperplasia mean scores in ventral prostate for the experiment described in FIG. 2.

At necropsy, the ventral and dorsolateral lobes of the prostate were separated and then cut into halves. The left halves were fixed in 10% neutral buffered formalin, sectioned, and stained with Hematoxylin and Eosin (H&E). Histological changes in these sections were scored. Epithelial hyperplasia was recognized as an increase in epithelial cells within normal-appearing gland profiles, primarily reflected by stratification of epithelial cells and increased presence of epithelial tufting and papillary projections. A severity grade of 0 (not present) through 5 (severe) was assigned to each sample. Representative images are presented in FIGS. 1 and 2. The mean scores (+/−SD) are shown in FIGS. 3 and 4.

FIG. 1 shows representative images from dorsolateral prostate at 100× magnifications. Panel (A) is a vehicle-treated sample, showing a normal (score=0) glandular profile. Panel (B) is a testosterone (TE) and phenylephrine (PE) induced and vehicle-treated sample, showing marked (score=4) epithelial hyperplasia. Panel (C) is a testosterone (TE) and phenylephrine (PE) induced and nintedanib-treated sample, showing moderate (score=3) epithelial hyperplasia. Panel (D) is a testosterone (TE) and phenylephrine (PE) induced and sunitinib-treated sample, showing moderate (score=3) epithelial hyperplasia. Panel (E) is a testosterone (TE) and phenylephrine (PE) induced and lenvatinib-treated sample, showing slight (score=2) epithelial hyperplasia. Panel (F) is a testosterone (TE) and phenylephrine (PE) induced and doxazosin-treated sample, showing moderate (score=3) epithelial hyperplasia.

Figure 2:
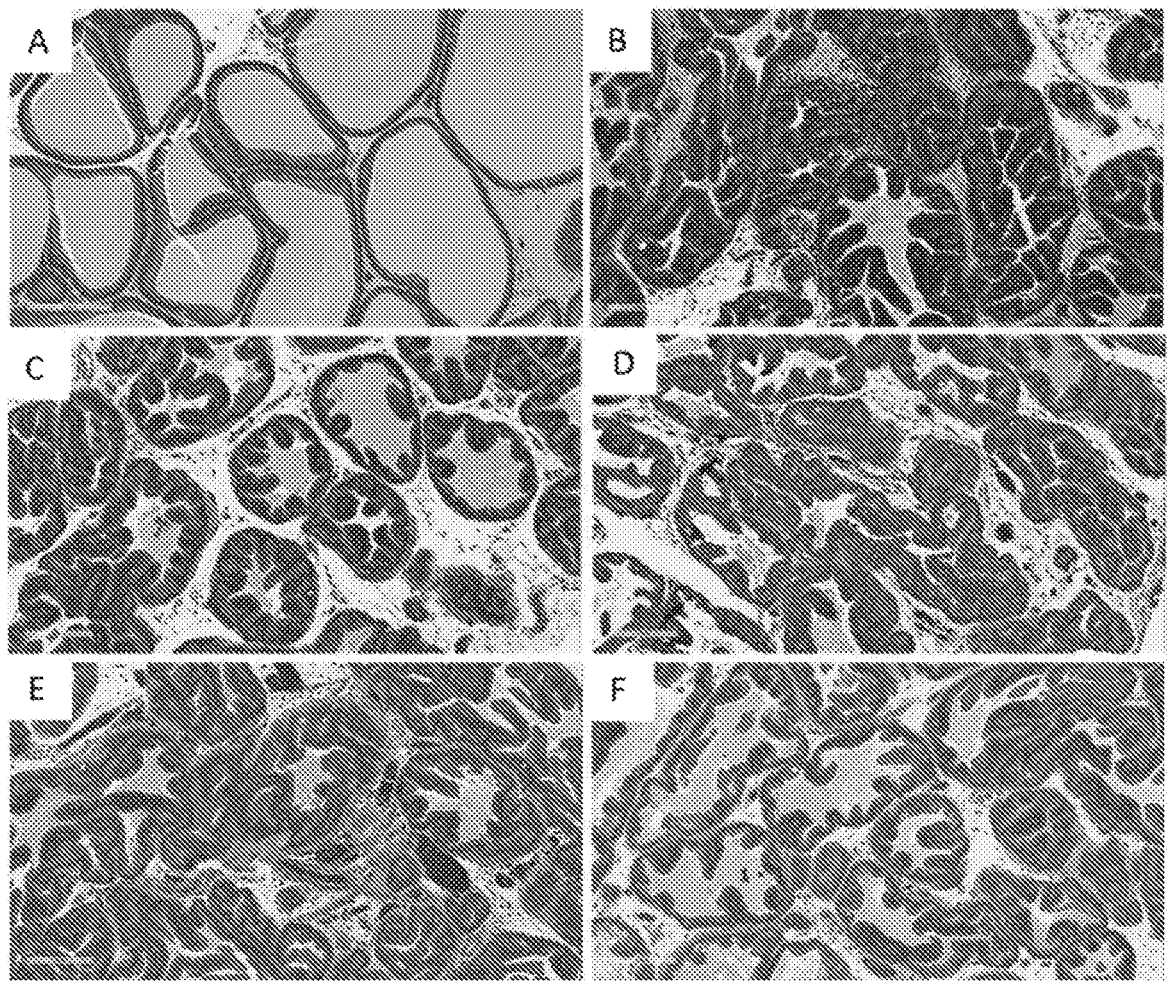
FIG. 2 shows representative images from ventral prostate at 100× magnification. Panel (A) is a vehicle-treated sample, showing a normal (score=0) glandular profile. Panel (B) is TE) and PE induced and vehicle-treated sample, showing marked (score=4) epithelial hyperplasia. Panel (C) is TE and PE induced and nintedanib-treated sample, showing moderate (score=3) epithelial hyperplasia. Panel (D) is TE and PE induced and sunitinib-treated sample, showing moderate (score=3) epithelial hyperplasia. Panel (E) is TE and PE induced and lenvatinib-treated sample, showing slight (score=3) epithelial hyperplasia. Panel (F) is TE and PE induced and doxazosin-treated sample, showing moderate (score=3) epithelial hyperplasia.

FIG. 2 shows representative images from ventral prostate at 100× magnification. Panel (A) is a vehicle-treated sample, showing a normal (score=0) glandular profile. Panel (B) is testosterone (TE) and phenylephrine (PE) induced and vehicle-treated sample, showing marked (score=4) epithelial hyperplasia. Panel (C) is testosterone (TE) and phenylephrine (PE) induced and nintedanib-treated sample, showing moderate (score=3) epithelial hyperplasia. Panel (D) is testosterone (TE) and phenylephrine (PE) induced and sunitinib-treated sample, showing moderate (score=3) epithelial hyperplasia. Panel (E) is testosterone (TE) and phenylephrine (PE) induced and lenvatinib-treated sample, showing slight (score=3) epithelial hyperplasia. Panel (F) is testosterone (TE) and phenylephrine (PE) induced and doxazosin-treated sample, showing moderate (score=3) epithelial hyperplasia.

The study results indicate histological changes of glandular hyperplasia after TE and PE induction in rats, which were observed in human prostate hyperplasia and adenoma, i.e., glandular hyperplasia forming papillary structures toward lumen Test compounds of nintedanib, Sunitinib, lenvatinib, and doxazosin demonstrated reduction of glandular hyperplasia as compared to the untreated TE/PE induced prostates (FIGS. 1B and 2B). Inhibition of benign prostate hyperplasia in this model by nintedanib, sunitinib, lenvatinib and doxazosin indicates that these compounds would be effective in the treatment of benign prostate hyperplasia (BPH) and proliferative and fibrotic disorders of the genitourinary tract.

Example 2

Morphologically, BPH is characterized by the formation of a new architecture through the proliferation of the epithelium in pre-existing ducts. Given that stromal cells serve important paracrine regulatory functions in epithelial cell homeostasis, late stage changes in stromal-epithelial interactions could provide insight into BPH progression. A second study was conducted to determine the therapeutic effects of test compounds and vehicle, post-induction in a protocol using testosterone and/or phenylephrine induced BPH in rats.

Male Wistar rats were induced with testosterone (2 mg/kg) plus phenylephrine (5 mg/kg) administered daily by subcutaneous injection on days 1 through 28. Vehicle or test compounds sorafenib (1% w/w), pirfenidone (2.5% w/w), and riociguat (1% w/w) were administered by intra-prostate injection (0.2 ml) in the dorsolateral lobe on days 15 and 29. Animals were euthanized on day 42. Body weights were determined. Prostate glands were harvested and weighed. The experimental design is outlined in Table 2.

TABLE 2

Study Design Outline

| Group (Test Article) | Dose | Route of Administration | Day(s) of Administration | Animal Numbers |
|---|---|---|---|---|
| 1 (vehicle) | 0 | Intra-prostate | 15, 29 | 6 |
| 2 (sorafenib) | 2 | Intra-prostate | 15, 29 | 8 |
| 3 (pirfenidone) | 5 | Intra-prostate | 15, 29 | 7 |
| 4 N/A | N/A | N/A | N/A | 5 |
| 5 N/A | N/A | N/A | N/A | 7 |
| 6 (riociguat) | 2 | Intra-prostate | 15, 29 | 7 |

For Groups 1 through 3, Testosterone and Phenylephrine was injected on days 1-28. For Groups 5 and 6, Testosterone was injected on days 1-28.

Figure 5:
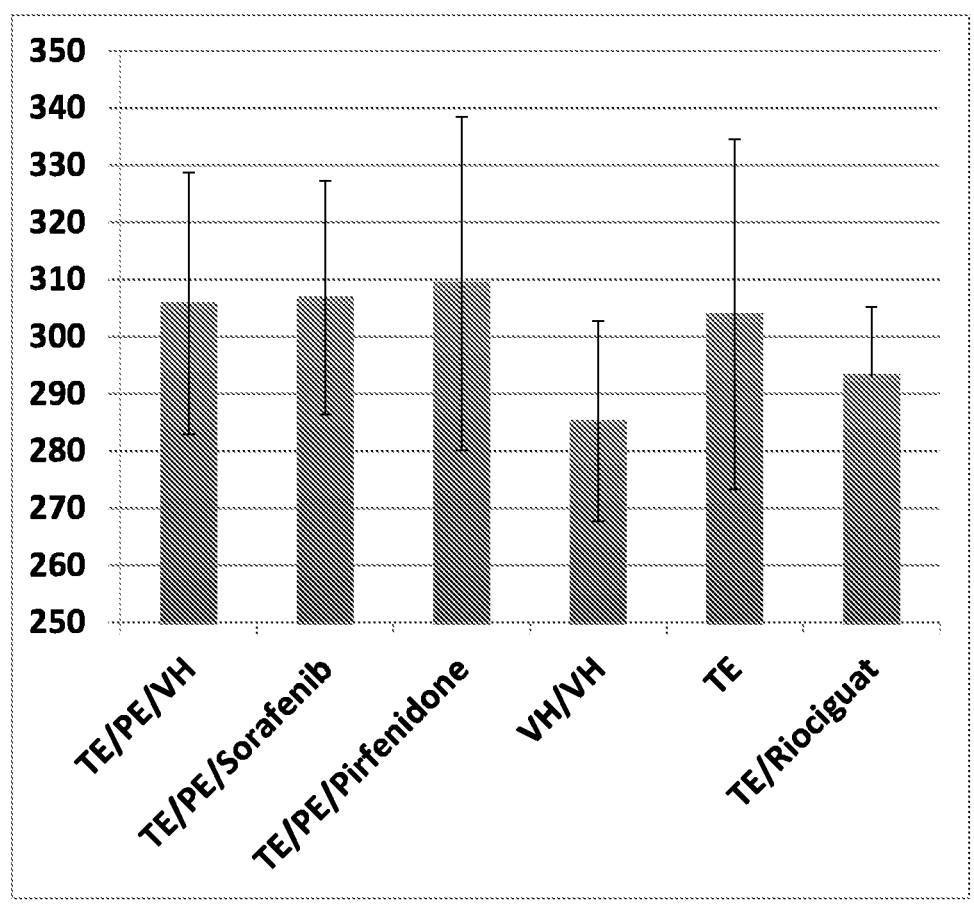
FIG. 5 shows prostate weights/100 g body weight for various treatment groups.

Prostate weight/100 g body weight was determined for each treatment group. As shown in FIG. 5, sorafenib and pirfenidone did not show a reduction in mean prostate weight compared to vehicle. In a similar test (with TE induction), riociguat treatment reduced the mean prostate weight, as compared to the vehicle control.

At necropsy, the dorsolateral and ventral lobes of the prostate were separated and cut into halves. The left halves were fixed in 10% neutral buffered formalin, sectioned, and stained with Hematoxylin and Eosin (H&E). Epithelial hyperplasia was recognized as an increase in epithelial cells within normal appearing gland profiles, as reflected in the stratification of epithelial cells and increased presence of epithelial tufting and papillary projections. Stromal changes were examined microscopically. These changes included inflammation and tissue fibroplasia. Each section was given a severity score ranging from 0 (not present) through 5 (severe).

Figure 6:
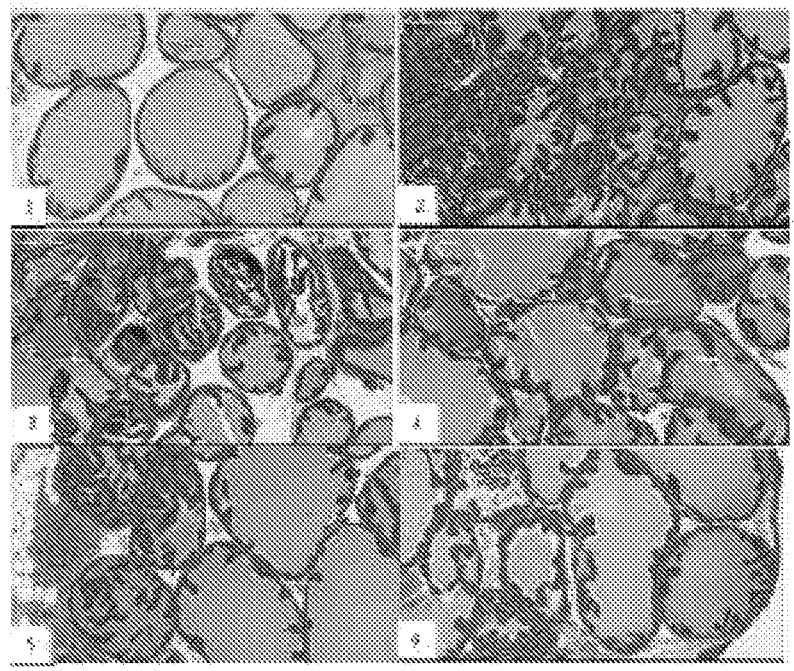
FIG. 6 shows representative images from dorsolateral prostate at 100× magnification. Panel (1) is the image of Group 5 (vehicle) rat showing normal (score=0) glandular profile. Panel (2) is the image of Group 1 (TE+PE induced and vehicle-treated) rat showing slight (score=2) epithelial hyperplasia. Panel (3) is the image of Group 3 (TE+PE induced and sorafenib 1%-treated) rat showing slight (score=2) epithelial hyperplasia. Panel (4) is the image of Group 4 (TE+PE induced and pirfenidone 2.5%-treated) rat showing minimal (score=1) epithelial hyperplasia. Panel (5) Group 6 is the image of (TE-induced) rat showing slight (score=2) epithelial hyperplasia. Panel (6) Group 7 (TE induced and riociguat 1%-treated) rat showing minimal (score=1) epithelial hyperplasia.
Figure 7:
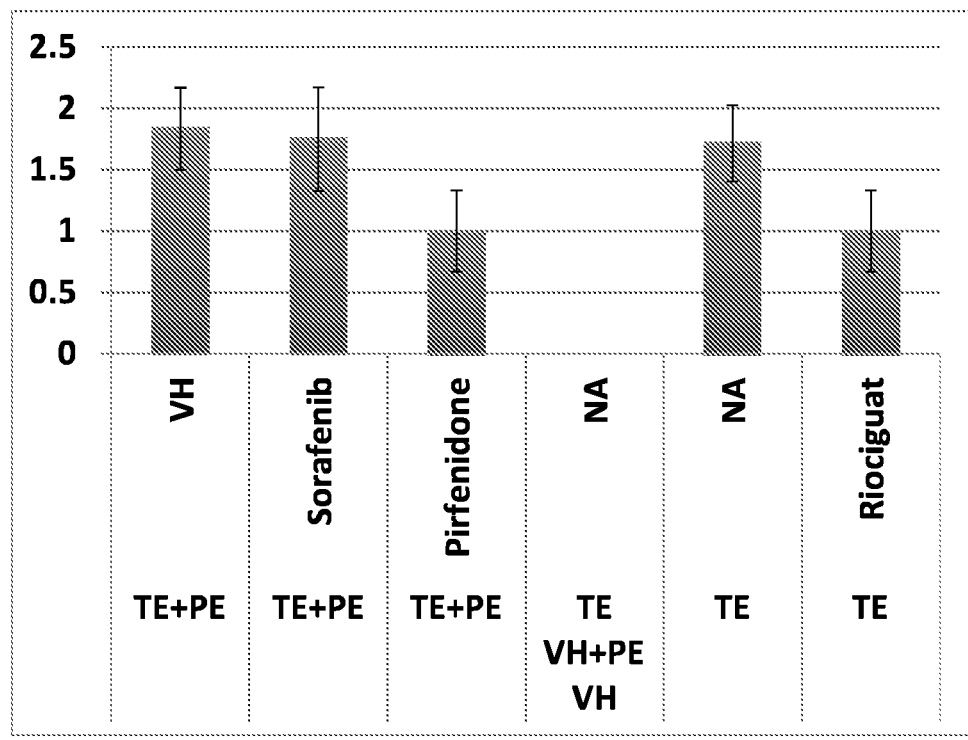
FIG. 7 shows epithelial hyperplasia mean scores in rat BPH model for the experiment described in FIG. 6.

FIG. 6 shows representative images from dorsolateral prostate at 100× magnification. Panel (1) is the image of Group 5 (vehicle) rat showing normal (score=0) glandular profile. Panel (2) is the image of Group 1 (TE+PE induced and vehicle-treated) rat showing slight (score=2) epithelial hyperplasia. Panel (3) is the image of Group 2 (TE+PE induced and sorafenib 1%-treated) rat showing slight (score=2) epithelial hyperplasia. Panel (4) is the image of Group 3 (TE+PE induced and pirfenidone 2.5%-treated) rat showing minimal (score=1) epithelial hyperplasia. Panel (5) Group 5 is the image of (TE-induced) rat showing slight (score=2) epithelial hyperplasia. Panel (6) Group 6 (TE induced and riociguat 1%-treated) rat showing minimal (score=1) epithelial hyperplasia. These scores are summarized in a bar graph, shown in FIG. 7.

This study shows that resolution of induced BPH in the rat model over time led to a reduction in the response to test compounds of pirfenidone and riociguat. Riociguat showed an effect on prostate volume and histological changes in epithelial hyperplasia. It was also observed that sorafenib, a multikinase inhibitors with anti-VEGFR and anti-PDGFR activity, was not an effective inhibitor of benign prostate hyperplasia. Therefore, not all multikinase inhibitors will offer preventive or therapeutic benefits in prostatic hyperplasia and/or fibrotic disorders.

Example 3

Prostate concentration of sorafenib after intraprostate injection in the rat.

In this study, single intraprostate injections of sorafenib were administered on Days 15 and 29. Animals were euthanized on Day 42 and prostate tissue samples were obtained for analysis. Tissue samples were prepared using a Bead Ruptor homogenizer, followed by extraction with acetonitrile and high-speed centrifugation. An LC-MS/MS method for measurement of sorafenib was used.

On day 42, the mean concentration in the prostate for sorafenib was 892 mg/gm. These tissue concentrations are higher than required for inhibition of VEGFR and PDGFR activity. This study supports the idea that despite good sorafenib exposure in the prostate, sorafenib did not show any therapeutic effect in the prostate.

Example 4

Fibroplasia is generally a late phase reactive and/or reparative response in tissues associated with disease, trauma, genetic disorders, or infection. There is a strong overlap in the pathophysiology regardless of the organ or tissue involved. Observations made in tissues other than prostate could contribute to our understanding of fibrotic disease progression and regression relevant to prostatic diseases or disorders, such as benign prostatic hyperplasia and its associated lower urinary tract symptoms.

A study was conducted to determine the potential beneficial effects of topical administration of test compounds and vehicle in a suture induced fibrosis model in rabbits. Sutures were placed intrastromally, under a microscope, in the cornea of rabbits. In each eye, one 9-0 silk suture was placed, in a vertical position, temporal to the center of the cornea and a second suture was placed nasal to the corneal center. Each suture had two stromal incursions approximately 2 mm from the limbus. Test compounds having a certain spectrum of multikinase inhibition activities, or vehicle, were topically instilled (35 µL/eye) in the eyes three times daily for 10 days following surgery. The treatment groups include vehicle, nintedanib (0.3%, w/w), sorafenib (0.3%, w/w) and lenvatinib (0.3%, w/w). Six left eyes were used per treatment group.

During the in-life phase, gross ocular observations of very slight to moderate conjunctival congestion and swelling were similar among groups, including the vehicle control.

The animals were sacrificed on Day 11 and eyes enucleated and dissected for histopathological evaluation. The results are shown in FIG. 8.

Figure 8:
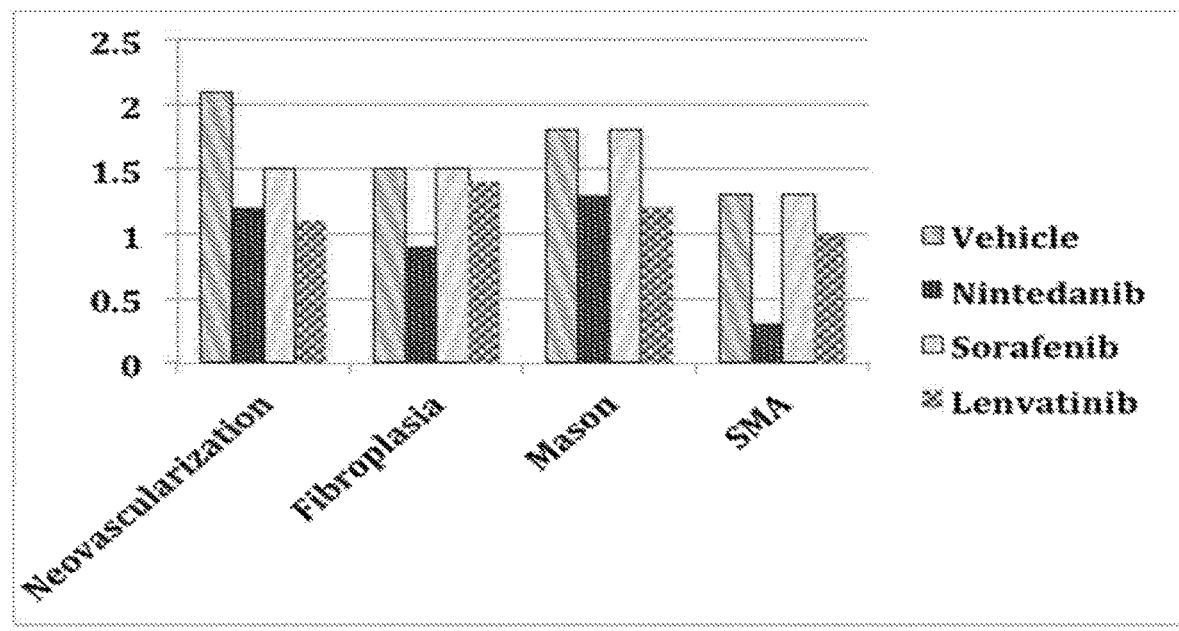
FIG. 8 shows histology findings in corneal suture fibrosis model, as described in Example 4.

The results show that nintedanib and lenvatinib significantly reduced fibroplasia and/or collagen density, as evidenced by histological staining (see FIG. 8). In contrast, sorafenib had little or no effect on fibroplasia or collagen formation, as revealed by Masson's trichrome test to differentiate cells from surrounding connective tissue, especially collagen formation in fibrotic responses. In addition, nintedanib and lenvatinib significantly reduced alpha SMA staining by immunohistochemical analysis, while sorafenib had no effect on alpha SMA relative to vehicle treatment. Alpha SMA is a key marker of myofibroblasts, whose function in wound healing and extracellular matrix formation is associated with fibrotic disease.

Example 5

Increased expression of angiogenic factors, such as VEGF and bFGF, along with increased microvessel density, have been reported in benign prostatic hyperplasia, high grade prostate intraepithelial neoplasia and prostate cancer. This suggests a role for inhibition of these factors in the regulation of BPH. In this example, the effect of local administration of multikinase inhibitors in a rat model of neovascularization was examined. New vessel growth is regulated by growth factor receptor signaling pathways, the functions of which broadly overlap among organs and tissues. In this study, effects of local administration of the multikinase inhibitors nintedanib and lenvatinib were examined by intravitreal injection or topical application to rat eyes following laser induced choroidal neovascularization.

A 22-day study was conducted to determine the effects of test agents, positive control, or vehicle on the development of new vessels. On Day 1, laser treatments were performed on all animals using a 520 nm thermal laser to generate a total of three lesions per eye. On Days 2-21, bilateral topical administration of vehicle, 1% nintedanib, or 1% lenvatinib was performed three times a day. On Day 3, bilateral intravitreal injection of vehicle, 5 µg/eye of rat anti-VEGF antibody, 50 µg/eye of nintedanib, or 50 µg/eye of lenvatinib was performed in a second group of animals.

Figure 9:
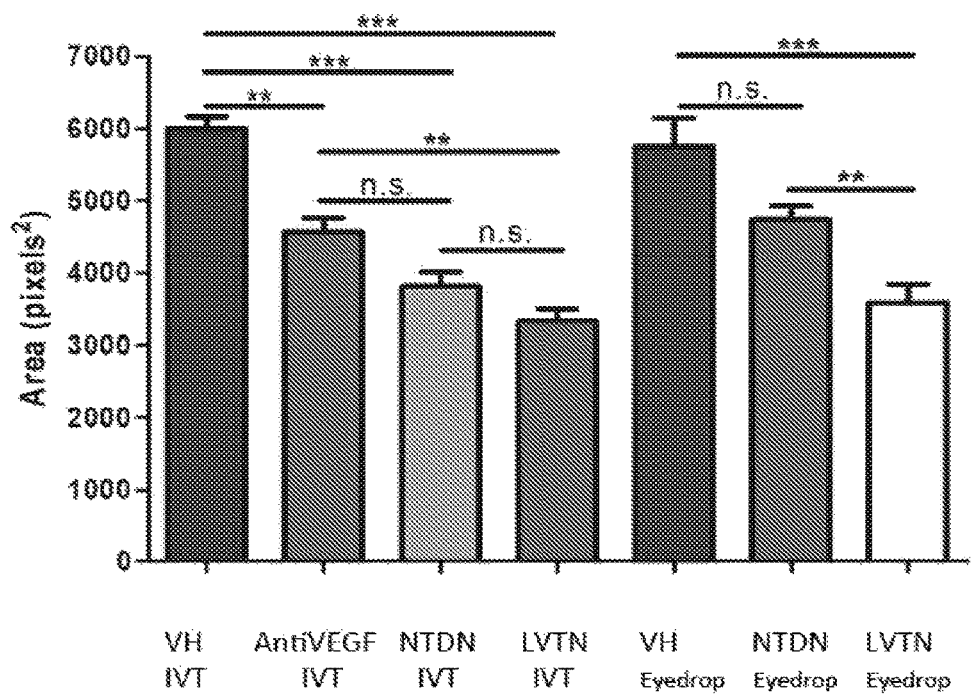
FIG. 9 shows reduction of neovascular lesions in rat choroidal neovascularization model, as described in Example 5.

On Day 22, fluorescein angiography was performed on all animals and lesion size/area was determined using image analysis software (ImageJ). As shown in FIG. 9, when delivered via intravitreal injections, nintedanib and lenvatinib treatments significantly reduced lesion sizes relative to those of the vehicle-treated eyes. In addition, intravitreal injection of lenvatinib also significantly reduced lesion sizes relative to those of the positive control, rat anti-VEGF.

In addition to intravitreal injection, compounds of the invention can also be used in topical application. As shown in FIG. 9, topical eyedrop administration of either nintedanib or lenvatinib reduced lesion sizes relative to those of the vehicle.

These data show that nintedanib and lenvatinib are effective in reducing neovascularization from laser-induced lesion after local administrations, e.g., injection or topical applications.

What is claimed is:

1. A method for treating and/or improving a prostatic disease or disorder associated with epithelial hyperplasia and/or fibrosis, comprising: administering an effective amount of a multikinase inhibitor to a subject in need thereof, wherein the multikinase inhibitor is lenvatinib.

2. The method according to claim 1, wherein the prostatic disease or disorder is benign prostate hyperplasia (BPH) or its associated lower urinary tract symptoms in animals and humans.

3. The method according to claim 1, wherein the prostatic disease or disorder is fibrosis of ureters and renal pelvis in animals and humans.

4. The method according to claim 1, wherein the prostatic disease or disorder is prostate adenoma in animals and humans.

5. The method according to claim 1, wherein the prostatic disease or disorder is prostatic intraepithelial neoplasia in animals and humans.

6. The method according to claim 1, wherein the multikinase inhibitor is administered by intra-prostate injection.

7. The method according to claim 1, wherein the multikinase inhibitor is administered by periprostatic injection.

8. The method according to claim 1, wherein the multikinase inhibitor is administered by transrectal delivery.

9. The method according to claim 1, wherein the multikinase inhibitor is administered by transurethral delivery.

10. The method according to claim 1, wherein the multikinase inhibitor is administered by parenteral delivery.

11. The method according to claim 1, wherein the multikinase inhibitor is administered by intraperitoneal, subcutaneous, intramuscular, intradermal, topical, intralesional, or perilesional delivery.

* * * * *